United States Patent
Keshtmand et al.

(10) Patent No.: US 10,792,313 B2
(45) Date of Patent: Oct. 6, 2020

(54) STABLE DRY COMPOSITIONS HAVING NO OR LITTLE SUGARS

(71) Applicant: Advanced Bionutrition Corp., Columbia, MD (US)

(72) Inventors: Majid Keshtmand, Baltimore, MD (US); Mordechai Harel, Pikesville, MD (US); Trisha Rice, Columbia, MD (US)

(73) Assignee: Advanced BioNutrition Corp., Columbia, MD (US)

( * ) Notice: Subject to any disclaimer, the term of this patent is extended or adjusted under 35 U.S.C. 154(b) by 72 days.

(21) Appl. No.: 15/776,467

(22) PCT Filed: Nov. 30, 2016

(86) PCT No.: PCT/US2016/064176
§ 371 (c)(1),
(2) Date: May 16, 2018

(87) PCT Pub. No.: WO2017/095897
PCT Pub. Date: Jun. 8, 2017

(65) Prior Publication Data
US 2018/0325967 A1 Nov. 15, 2018

Related U.S. Application Data

(60) Provisional application No. 62/263,061, filed on Dec. 4, 2015.

(51) Int. Cl.
| | | |
|---|---|---|
| *A61K 35/745* | (2015.01) | |
| *A23K 10/18* | (2016.01) | |
| *A23L 33/135* | (2016.01) | |
| *A23K 40/30* | (2016.01) | |
| *A23K 50/75* | (2016.01) | |
| *A23K 50/42* | (2016.01) | |
| *A23K 50/80* | (2016.01) | |
| *C12N 1/20* | (2006.01) | |
| *A61K 35/66* | (2015.01) | |
| *A23K 40/25* | (2016.01) | |
| *A61K 35/744* | (2015.01) | |
| *A23K 20/158* | (2016.01) | |
| *C12N 1/04* | (2006.01) | |
| *A23K 20/147* | (2016.01) | |
| *A23K 20/163* | (2016.01) | |
| *A23K 20/174* | (2016.01) | |
| *A23K 20/105* | (2016.01) | |
| *A23L 33/18* | (2016.01) | |

(Continued)

(52) U.S. Cl.
CPC .......... *A61K 35/745* (2013.01); *A23K 10/18* (2016.05); *A23K 20/105* (2016.05); *A23K 20/147* (2016.05); *A23K 20/158* (2016.05); *A23K 20/163* (2016.05); *A23K 20/174* (2016.05); *A23K 40/25* (2016.05); *A23K 40/30* (2016.05); *A23K 50/42* (2016.05); *A23K 50/75* (2016.05); *A23K 50/80* (2016.05); *A23L 2/66* (2013.01); *A23L 33/125* (2016.08); *A23L 33/135* (2016.08); *A23L 33/15* (2016.08); *A23L 33/18* (2016.08); *A23L 33/185* (2016.08); *A23L 33/19* (2016.08); *A23L 33/40* (2016.08); *A61K 35/66* (2013.01); *A61K 35/742* (2013.01); *A61K 35/744* (2013.01); *A61K 35/76* (2013.01); *C12N 1/04* (2013.01); *C12N 1/20* (2013.01); *A23V 2002/00* (2013.01); *A23Y 2220/03* (2013.01); *A23Y 2220/17* (2013.01); *A61K 2035/115* (2013.01); *Y02A 40/818* (2018.01)

(58) Field of Classification Search
None
See application file for complete search history.

(56) References Cited

U.S. PATENT DOCUMENTS

| | | |
|---|---|---|
| 6,653,062 B1 | 11/2003 | DePablo et al. |
| 8,853,148 B2 | 10/2014 | Miller et al. |

(Continued)

FOREIGN PATENT DOCUMENTS

| | | |
|---|---|---|
| CN | 103347395 A | 10/2013 |
| JP | 2013521779 A | 6/2013 |

(Continued)

OTHER PUBLICATIONS

Extended European Search Report for European Application No. 16 871 407.9, dated Jun. 3, 2019, 8 pages.

(Continued)

*Primary Examiner* — Heidi Reese
(74) *Attorney, Agent, or Firm* — RatnerPrestia

(57) ABSTRACT

A dry stable composition is provided. The composition comprises one or more viable microorganisms, at least 50% by weight of one or more hydrolyzed proteins and less than 10% by weight of one or more sugars selected from the group consisting of monosaccharides, disaccharides and combinations thereof, each weight percentage based on the total weight of the dry composition. Preferably, the composition comprises no monosaccharide or disaccharide. The composition may further comprise one or more oligosaccharides, one or more polysaccharides, one or more carboxylic acid salts, or a combination thereof. The composition may have viability of at least $1 \times 10^{10}$ CFU/g, and a viability loss of less than 1 log unit/g after 84 days at a temperature of 40° C. and a relative humidity of 33%. Also provided are methods for preparing the dry stable composition.

23 Claims, 2 Drawing Sheets

(51) Int. Cl.
  *A23L 33/19*     (2016.01)
  *A23L 33/125*    (2016.01)
  *A23L 33/15*     (2016.01)
  *A23L 33/185*    (2016.01)
  *A23L 33/00*     (2016.01)
  *A23L 2/66*      (2006.01)
  *A61K 35/742*    (2015.01)
  *A61K 35/76*     (2015.01)
  *A61K 35/00*     (2006.01)

(56) References Cited

U.S. PATENT DOCUMENTS

| | | | |
|---|---|---|---|
| 8,871,266 | B2 | 10/2014 | Crittenden et al. |
| 9,504,750 | B2 * | 11/2016 | Harel .................... A61K 47/40 |
| 2003/0194423 | A1 | 10/2003 | Torney et al. |
| 2007/0258965 | A1 | 11/2007 | Remaut et al. |
| 2010/0189767 | A1 | 7/2010 | Shimoni et al. |
| 2011/0070334 | A1 | 3/2011 | Rangavajla |
| 2012/0135017 | A1 | 5/2012 | Harel et al. |
| 2013/0287896 | A1 | 10/2013 | Harel et al. |
| 2013/0296165 | A1 | 11/2013 | Harel et al. |
| 2013/0323362 | A1 | 12/2013 | Penhasi |
| 2013/0344045 | A1 | 12/2013 | Faure et al. |

FOREIGN PATENT DOCUMENTS

| | | |
|---|---|---|
| JP | 2015517985 A | 6/2015 |
| WO | 2013142792 A1 | 9/2013 |
| WO | 2017019273 A1 | 2/2017 |

OTHER PUBLICATIONS

Schnaider-Beeri et al., The Journal of the Alzheimer's Association, 2(3) Supp.:S406, 7 pages (2006).
Giulio et al., World Journal of Microbiology & Biotechnology, 21:739-46 (2005).
Hubálek, Cryobiology, 46:205-29 (2003).
International Search Report for International Application No. PCT/US2016/064176 dated Mar. 13, 2017.
Kanmani et al., Biochemical Engineering Journal, 58-59:140-47 (2011).
Morgan et al., Journal Microbiological Methods, 66:183-93 (2006).
Nag and Das, International Journal of Dairy Technology, 66(2):162-69 (2013).
International Preliminary Report on Patentability and Written Opinion for International Application No. PCT/US2016/064176, dated Jun. 5, 2018, 9 pages.
Japanese Notice of Reasons for Refusal for Japanese Application No. 2016-548644, dated Aug. 19, 2020 with translation, 8 pages.
Brazilian Office Action for Brazilian Application No. 112018010789-1, dated Aug. 11, 2020 with partial translation, 5 pages.

* cited by examiner

STABLE DRY COMPOSITIONS HAVING NO OR LITTLE SUGARS

This application is a U.S. National Phase Application of PCT International Application No. PCT/US2016/064176, filed Nov. 30, 2016, related to and claims the benefit of U.S. Provisional Application No. 62/263,061, entitled STABLE DRY COMPOSITIONS HAVING NO OR LITTLE SUGARS filed on Dec. 4, 2015, the contents of each of which are incorporated herein by reference.

FIELD OF THE INVENTION

The present invention relates to stable dry compositions for viable microorganisms having no or little sugars (i.e., monosaccharides and/or disaccharides) and preparation methods thereof.

BACKGROUND OF THE INVENTION

There are currently a variety of microorganisms for supplementing gastrointestinal tracts of animals, including humans. These microorganisms may modulate a natural microflora within an animal's gut for a desirable biological effect.

One of the challenges to providing an effective amount of live microorganisms to a host is the preservation of their viability under the harsh conditions of typical industrial manufacturing processes and long-term storage at high temperature and humidity. Although there have been developments concerning encapsulation and formulation techniques for delivery of biological materials into digestive systems of animals, there has been little development in encapsulation or stabilization techniques that protect the viability of live microorganisms during manufacturing processes, distribution and storage. There is a need for a composition and stabilization technique that enables live microorganisms to survive upon exposure to various harsh environments, especially those associated with elevated temperature and humidity.

In addition, the inherent moisture of a consumable product itself poses another challenge in that live microorganisms generally are sensitive to water activity, especially in combination with high temperature. To date, no technology or technique has been identified to provide significant protection of live microorganisms under intermediate moisture conditions (i.e., water activity of about 0.2 and higher, or up to about 0.4 or higher) and high temperatures during distribution and storage (e.g., temperatures of at least about 30° C., or up to about 40° C. or higher) when incorporated into products such as nutritional products and animal feeds. As such, there is a need for stable live microorganism compositions suitable for distribution in various geographic locations, including those in tropical climates, where the viability of probiotics could be compromised.

Additional challenges include nutritional and regulatory limitations on the use of conventional food ingredients suitable for consumption by specific groups of people like infants, young children, elderly people and diabetic people that are limited to a sugar-less diet. Conventional synthetic encapsulation and stabilizing compounds and even some natural compounds such as milk proteins and certain sugars such as sucrose, fructose, trehalose and lactose are not recommended for use in these special dietary formulations. A recommended list of nutritional compounds allowed for special dietary uses is regulated by the joint FAO/WHO Codex Alimentarius Commission.

What is desired therefore is stable dry compositions comprising live microorganisms such as probiotic bacteria and other suitable ingredients, and stabilization techniques for making such compositions.

SUMMARY OF THE INVENTION

The present invention relates to stable dry compositions having no or little sugars (i.e., monosaccharides and/or disaccharides), and preparation thereof. Unless stated otherwise, all percentages by weight (wt %) of ingredients in a composition are based on the total weight of the composition.

A dry composition is provided. The composition comprises one or more viable microorganisms, at least 50% by weight of one or more hydrolyzed proteins and less than 10% by weight of one or more sugars selected from the group consisting of monosaccharides, disaccharides and combinations thereof, each percentage based on the total weight of the dry composition. The composition may further comprise one or more oligosaccharides, one or more polysaccharides, one or more carboxylic acid salts, or a combination thereof. The one or more viable microorganisms may be selected from the group consisting of live bacteria, fungi, yeast, unicellular algae, viruses and phages.

The one or more hydrolyzed proteins may be milk proteins, plant proteins, or combinations thereof. The one or more hydrolyzed proteins may be selected from the group consisting of hydrolyzed casein, hydrolyzed whey protein, hydrolyzed pea protein, hydrolyzed soy protein, and combinations thereof.

The composition may further comprise 5-30% by weight of one or more oligosaccharides based on the total weight of the dry composition. The one or more oligosaccharides may be selected from the group consisting of inulin, short chain oligosaccharides, cyclodextrins, maltodextrins, dextrans, fructo-oligosaccharides (FOS), galacto-oligosaccharides (GOS), mannan-oligosaccharides (MOS), and combinations thereof. The one or more oligosaccharides may be inulin, short chain oligosaccharides or cyclodextrin.

The composition may further comprise 1-10% by weight of one or more polysaccharides based on the total weight of the dry composition. The one or more polysaccharides may be selected from the group consisting of alginate, gum acacia, locust bean gum, carrageenan, starches, modified starches, and combinations thereof.

The composition may further comprise 1-10% by weight of one or more carboxylic acid salts based on the total weight of the dry composition. The one or more carboxylic acid salts may be one or more salts of a carboxylic acid selected from the group consisting of lactic acid, ascorbic acid, maleic acid, oxalic acid, malonic acid, malic acid, succinic acid, citric acid, gluconic acid, glutamic acid, and combinations thereof. The one or more carboxylic acid salts may be selected from the group consisting of ascorbic acid salts, citric acid salts, and combinations thereof.

The composition may further comprise 1-5% by weight of vitamin E based on the total weight of the dry composition. The composition may have viability of at least $1 \times 10^{10}$ CFU/g, and a viability loss of less than 1 log unit/g after 84 days at a temperature of 40° C. and a relative humidity of 33%. The one or more hydrolyzed protein may be hydrolyzed pea protein or hydrolyzed casein.

A method is provided for preparing a dry composition comprising one or more viable microorganisms, at least 50% by weight of one or more hydrolyzed proteins based on the total weight of the dry composition, one or more oligosaccharides, one or more polysaccharides, and one or more carboxylic acid salts. The method comprises (a) combining the one or more viable microorganisms, the one or more hydrolyzed proteins, the one or more oligosaccharides, the one or more polysaccharides and the one or more carboxylic acid salts in an alkali aqueous solvent to form a slurry; (b) snap-freezing the slurry in liquid nitrogen to form solid frozen particles in the form of beads, droplets or strings; (c) primary drying the solid frozen particles by evaporation, under vacuum, while maintaining the temperature of the particles above their freezing temperature, whereby a primarily dried formulation is formed; and (d) secondary drying the primarily dried formulation at full strength vacuum and a heat source temperature of 20° C. or higher for a time sufficient to reduce the water activity of the primarily dried formulation to 0.3 Aw or lower, whereby the composition is prepared. Preferably, no monosaccharide or disaccharide is added in the preparation method.

The method may further comprise adding one or more sugars to the alkali aqueous solvent to form the slurry in step (a), wherein the one or sugars are selected from the group consisting of monosaccharides, disaccharides and combinations thereof, and the resulting dry composition comprises less than 10% by weight of the one or more sugars based on the total weight of the dry composition. The method may further comprise sterilizing the one or more hydrolyzed proteins, the one or more oligosaccharides, the one or more polysaccharides, the one or more carboxylic acid salts, and the one or sugars before step (a).

The method may further comprise making a product with the composition, and the product is selected from the group consisting of pharmaceutical products, nutraceutical products, food products, feed products, and special dietary products. The special dietary product may be an infant formula, a follow-on formula, processed cereal based food, canned baby food, or special food for a medical purpose.

DETAILED DESCRIPTION OF THE INVENTION

Figure 1:
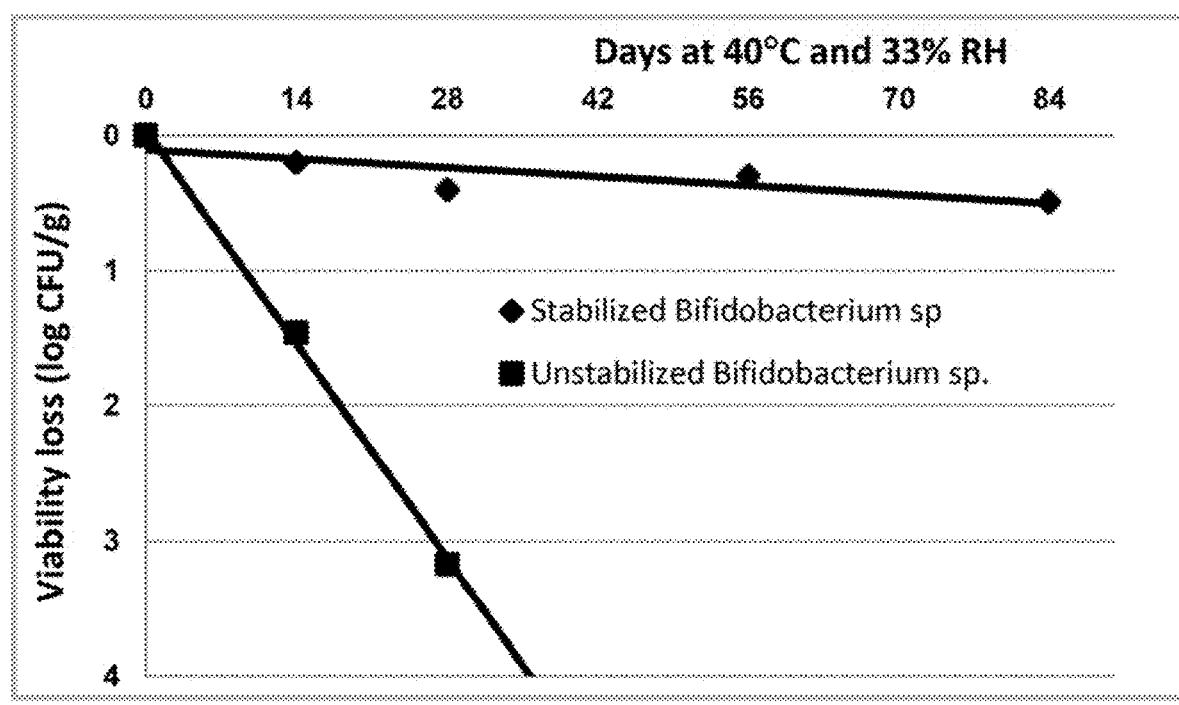
FIG. 1 shows storage stability of stabilized and unstabilized dry probiotic products prepared according to Examples 1 and 2, respectively, under accelerated storage conditions of 40° C. and 33% RH.

The present invention provides novel stable dry compositions containing no or little sugars (i.e., monosaccharides and/or disaccharides) and methods for making such compositions. These compositions provide surprisingly better stability and protection to viable microorganisms. The viable microorganisms may be protected during manufacturing processes for making consumable products, through distribution channels, and under extreme storage conditions. For example, most probiotic microorganism formulators over formulate their products with an extremely high count of bacterial cells, which may sometimes be as high as 10 and even 100 times more than an effective dose, with the understanding that a significant number of the cells ultimately lose viability and die during the manufacturing processes, transportation, and storage.

A stable dry composition is provided. The composition comprises one or more viable microorganisms and one or more hydrolyzed proteins, but no or little monosaccharides, disaccharides or a combination thereof. The dry composition may further comprise one or more oligosaccharides, one or more polysaccharides, one or more carboxylic acid salts, or a combination thereof. Preferably, the composition comprises at least about 50% by weight of the one or more hydrolyzed proteins and less than about 10% by weight of one or more sugars selected from the group consisting of monosaccharides, disaccharides and combinations thereof, each percentage based on the total weight of the dry composition. More preferably, the composition comprises less than about 5%, 1% or 0.1% by weight of one or more sugars selected from the group consisting of monosaccharides, disaccharides and combinations thereof. Most preferably, the composition comprises no monosaccharide or disaccharide.

Each ingredient in a dry composition may be measured in percentage by weight based on the total dry weight of the composition (w/w).

The term "carbohydrate" as used herein refers to an organic compound predominantly composed of carbon, hydrogen, and oxygen. A carbohydrate may be a monosaccharide, disaccharide, oligosaccharide or polysaccharide. An oligosaccharide and a polysaccharide typically composed of a sugar backbone of repeating structural units linked in linear or nonlinear fashion, some of which contain positively or negatively charged chemical groups. The repeating units may range from three to several million. Useful carbohydrates include reducing and non-reducing sugars and sugar alcohols, disaccharides, oligosaccharides, water soluble polysaccharides and derivatives thereof.

The term "sugar" as used herein refers to a monosaccharide or a disaccharide.

The term "monosaccharide" as used herein refers to a simplest form of a carbohydrate consisting of a single unit of sugar. Examples of suitable monosaccharides include glucose, fructose, and galactose.

The term "disaccharide" as used herein refers to a sugar having two monosaccharides linked together. The monosaccharides in a disaccharide may be the same or different. Examples of suitable disaccharides include sucrose, trehalose, lactose, maltose, isomaltose.

The term "oligosaccharide" as used herein refers to a carbohydrate having a small number of sugar units, typically 3-60 units, of monosaccharides linked together. An oligosaccharide containing less than 9 units of monosaccharides is also known as a short chain oligosaccharide. The monosaccharides in the oligosaccharide chain may be the same or different. Oligosaccharides are soluble fibers often considered as prebiotics in nutritional applications. Advantageously, soluble fibers pass through the stomach undigested and become available for digestion by the gut microflora. The incorporation of soluble fibers may also help to protect viable microorganisms from digestive enzymes and high acidity of the stomach. A commercial oligosaccharide product may contain monosaccharides and/or disaccharides. Examples of suitable oligosaccharides include inulin, maltodextrins, cyclodextrins, dextrans, fructo-oligosaccharides (FOS), galacto-oligosaccharides (GOS), mannan-oligosaccharides (MOS) and combinations thereof. Preferably, the oligosaccharide is inulin, short chain oligosaccharides, cyclodextrins or maltodextrins. More preferably, the oligosaccharide is inulin.

The term "polysaccharide" as used herein refers to a carbohydrate having a large number, typically more than 60 units, of monosaccharides linked together. The monosaccharides in a polysaccharide may be the same or different.

Examples of suitable polysaccharides include methylcellulose, hydroxypropylcellulose, hydroxyethylcellulose, and hypromellose; soluble starches or starch fractions, xanthan gum, guar gum, pectins, carrageen, galactomannan, gellan gum, including any derivatives of these, cellulose acetate phthalate (CAP), carboxy-methyl-cellulose, salts of alginic acid (e.g., sodium alginate), hydroxyl propyl methyl cellulose (HPMC), gum acacia, locust bean gum, chitosan and chitosan derivatives, collagen, polyglycolic acid, starches and modified starches and cyclodextrins. The polysaccharides may be selected from the group consisting of alginate, carrageenan, guar gum, gum acacia, locust bean gum, starch, modified starch, and combinations thereof, preferably alginate, gum acacia, locust bean gum, carrageenan, starches, modified starches, and combinations thereof, more preferably alginate, locust bean gum and guar gum.

A dry substance is a substance that is dehydrated or anhydrous, e.g., substantially lacking liquid. The dry substance, for example, a composition of the present invention, may be dried by one or more drying processes, for example, air drying, vacuum drying, fluidized bed drying, spray drying, and lyophilization.

The term "water activity (Aw)" as used herein refers to the availability of water in a substance, for example, a composition of the present invention, which represents the energy status of water in the substance. It may be defined as the vapor pressure of water above a substance divided by that of pure water at the same temperature. Pure distilled water has a water activity of exactly one, i.e., Aw=1.0. A dry substance may have an Aw of about 0.5 or lower, preferably about 0.3 or lower, more preferably about 0.2 or lower, most preferably about 0.1 or lower.

The term "viable microorganism" as used herein refers to a live microorganism that provides or confers a biological benefit, including an immunogenic response, to a host when administered to the host in an effective amount. The term "effective amount" as used herein refers to an amount of a viable microorganism that is sufficient to achieve a desirable biological benefit in a host when administered to the host via, for example, a pharmaceutical product, a nutraceutical supplement product, a dietary product, or an animal feed product. The viable microorganism may be selected from the group consisting of live bacteria, fungi, yeast, microalgae, viruses and phages. The desirable biological benefit may be any beneficial health, prophylactic, or nutritional effect, for example, maintaining a healthy gastrointestinal flora, enhancing growth, enhancing reproduction, enhancing immunity, preventing diseases, allergies and cold, or protecting against diarrhea, atopic dermatitis, or urinary infection.

The composition may comprise about 1-30%, 10-25%, 10-20% or 15-20% by weight of one or more viable microorganisms. The viable microorganisms may be live bacteria, fungi, yeast, unicellular algae, viruses, phages or a combination thereof. The bacteria may be probiotic bacteria or non-probiotic bacteria. The non-probiotic bacteria may be attenuated pathogenic bacteria. Suitable microorganisms include, but are not limited to, micro algae including any marine or fresh water species, yeasts such as *Saccharomyces, Debaromyces, Candida, Pichia* and *Torulopsis*; moulds such as *Aspergillus, Rhizopus, Mucor, Penicillium* and *Torulopsis*; and bacteria such as the genera *Bifidobacterium, Clostridium, Fusobacterium, Melissococcus, Propionibacterium, Streptococcus, Enterococcus, Lactococcus, Staphylococcus, Peptostrepococcus, Bacillus, Pediococcus, Micrococcus, Leuconostoc, Weissella, Aerococcus, Oenococcus* and *Lactobacillus*. Specific examples of suitable probiotic microorganisms may be represented by the following species and include all culture biotypes within those species: *Aspergillus niger, A. oryzae, Bacillus coagulans, B. lentus, B. licheniformis, B. mesentericus, B. pumilus, B. subtilis, B. natto, Bacteroidesamylophilus, Bac. capillosus, Bac. ruminocola, Bac. suis, Bifidobacteriumadolescentis, B. animalis, B. breve, B. bifidum, B. infantis, B. lactis, B. longum, B. pseudolongum, B. thermophilum, Candida pintolepesii, Clostridium butyricum, Enterococcus cremoris, E. diacetylactis, E. faecium, E. intermedius, E. lactis, E. muntdii, E. thermophilus, Escherichia coli, Kluyveromycesfragilis, Lactobacillus acidophilus, L. alimentarius, L. amylovorus, L. crispatus, L. brevis, L. case L. curvatus, L. cellobiosus, L. delbrueckii ss. bulgaricus, L farciminis, L. fermenturn, L. gasseri, L. helveticus, L. lactis, L. plantarum, L. johnsonii, L. reuteri, L. rhamnosus, L. sakei, L. salivarius, Leuconostocmesenteroides, P. cereviseae (damnosus), Pediococcusacidilactici, P. pentosaceus, Propionibacteriumfreudenreichii, Prop. shermanii, Saccharomyces cereviseae, Staphylococcus carnosus, Staph. xylosus, Streptococcus infantarius, Strep. salivarius. thermophilus, Strep. Thermophilus* and *Strep. Lactis*, and viruses or phages. Preferably, the probiotic bacteria are lactic acid bacteria and bifido bacteria.

The composition may comprise an effective amount of one or more viable microorganisms for providing a biological, or probiotic, benefit to a host in a pharmaceutical product, a nutraceutical supplement product, a dietary product, or an animal feed product, for example, a special dietary product such as an infant formula, a follow-on formula, processed cereal based food, canned baby food, or special food for a medical purpose.

The term "special dietary use" as used herein refers to making or applying a special dietary product to a host. Preferably, the special dietary product is recommended by the joint FAO/WHO Codex Alimentarius Commission in a document entitled "Standard For Infant Formula and Formulas For Special Medical Purposes Intended for Infants, CODEX STAN 72-1981" ("US Standard Codex 72"). Examples of a special dietary product include an infant formula, a follow-on formula, processed cereal based food, canned baby food, and special food for a medical purpose. Preferably, the special dietary product is an infant formula.

The host may be any animal, including a mammal, a human or an animal. The host may be an infant, a child or an elderly person. The term "infant" as used herein refers to a human from birth to about 12 months old. The term "child" as used herein refers to a human from about 12 months old to about 12 years old. The term "elderly person" as used herein refers to a human at least about 55, 60, 65 or 70 years old, preferably at least about 65 years old.

The composition may comprise at least about 40%, 45%, 50%, 55%, 60%, 65%, 75% or 80%, preferably at least about 50%, more preferably at least about 60%, by weight of one or more hydrolyzed proteins. For example, the composition may comprise about 40-80%, 40-70%, 50-60%, 50-70%, 50-75% or 50-80%, preferably 40-80°/0, by weight of hydrolyzed proteins.

The terms "hydrolyzed protein" and "protein hydrolysate" are used herein interchangeably, and refer to proteins broken down by hydrolysis or digestion into shorter peptide fragments and/or amino acids. The hydrolysis or digestion may be carried out by a strong acid, a strong base, an enzyme or a combination thereof. The hydrolyzed protein may be from an animal or a plant. The hydrolyzed proteins may be milk proteins, plant proteins, or a mixture thereof.

The hydrolyzed protein may be partially or extensively hydrolyzed, preferably extensively hydrolyzed. The hydrolyzed protein may be a mixture of polypeptides and amino acids. In some embodiments, at least about 60%, 70%, 80%, 90%, 95% or 99%/0, preferably at least about 75%, by weight of the hydrolyzed protein has a molecular weight lower than about 100,000, 75,000, 50,000, 25,000, 10,000, 5,000, 1,000 or 500 Dalton, preferably about 50,000 Dalton, more preferably about 10,000 Dalton, more preferably about 2,000 Dalton. For example, at least about 50%, 60%, 70%, 80% or 90%, preferably at least about 70%, by weight of the hydrolyzed protein has a molecular weight lower than about 2,000 Daltons.

Proteins suitable for making hydrolyzed proteins for the composition of the present invention include milk proteins, plant proteins, and combinations thereof. For example, suitable proteins include egg proteins, gelatin, milk proteins, casein, whey protein, albumen, soy protein, pea protein, rice protein, wheat protein, and other plant proteins. Preferably, the proteins are those recommended for non-allergenic dietary uses.

Examples of the hydrolyzed proteins include hydrolyzed casein, hydrolyzed whey protein, hydrolyzed pea protein, hydrolyzed soy protein, and combinations thereof. In one embodiment, the hydrolyzed protein comprises hydrolyzed casein or pea proteins, at least about 80% of which has a molecular weight of less than about 2,000 Daltons.

The composition may comprise a carbohydrate mixture of oligosaccharides and polysaccharides, in which the viable microorganism is embedded. A matrix may be formed by combining the carbohydrate mixture and extensively hydrolyzed proteins to allow faster drying and contribute to a desirable amorphous and rigid structure of the resulting dry composition.

The composition may comprise about 1-30%, 1-20%, 1-10%, 5-30%, 5-20%, 5-10%, 10-15%, 10-20% or 10-25% by weight of one or more oligosaccharides. Preferably, the composition comprises about 5-30% by weight of one or more oligosaccharides.

The composition may comprise about 0.1-40%, 0.5-30%, 1-30%, 1-20%, 1-10%, 1-5% or 5-10% by weight of one or more polysaccharides. Preferably, the composition comprises about 1-10% by weight of one or more polysaccharides.

The composition may comprise 0.1-20%, 0.5-20%, 1-20%, 0.1-10%, 0.5-10%, 1-10% or 1-5% by weight of one or more carboxylic acid salts, esters or derivatives thereof. The terms "carboxylic acid", "carboxylic salt", "carboxylic ester" and "carboxylic acid derivative" are used here interchangeably and refers to any organic compound that contains a carboxyl group (—COO$^-$). This component may provide enhanced matrix stability to the composition, and an additional benefit to viable microorganisms, a host or both. For example, this component may provide a therapeutic or immunogenic effect to a host who receives the composition. Suitable carboxylic acids may be selected from the group consisting of lactic acid, ascorbic acid, maleic acid, oxalic acid, malonic acid, malic acid, succinic acid, citric acid, gluconic acid, glutamic acid and a combination thereof. Suitable salts may include cations such as sodium, potassium, calcium, magnesium and a combination thereof. Examples of suitable carboxylic acid salts include sodium citrate, sodium lactate, sodium maleate, magnesium gluconate and sodium ascorbate, preferably salts of citric acid or ascorbic acid (e.g., sodium or potassium citrate, trisodium citrate dehydrate).

The composition may further comprise one or more additional agents. For example, the composition may further comprise 1-5% by weight of vitamin E based on the total weight of the composition.

In one embodiment, the composition comprises about 50-80% by weight of hydrolyzed proteins, about 5-30% by weight of oligosaccharides, about 1-10% by weight of polysaccharides, about 1-10% by weight of carboxylic acid salts, and less than about 10% by weight of one or more sugars selected from the group consisting of monosaccharides, disaccharides, and combinations thereof, preferably no monosaccharide or disaccharide.

In another embodiment, the composition comprises about 50-75% by weight of hydrolyzed pea protein, about 10-25% by weight of inulin, about 1-5% by weight of locust bean gum, about 1-10% by weight of one or more carboxylic acid salts selected from the group consisting of sodium citrate, sodium or potassium ascorbate, and combinations thereof, and less than about 10% by weight of one or more sugars selected from the group consisting of monosaccharides, disaccharides, and combinations thereof, preferably no monosaccharide or disaccharide.

The term "viability" as used herein refers to the ability of a microorganism in a composition to form colonies or viral plaques on a nutrient media appropriate for the growth of the microorganism, and may be expressed as colony forming units (CFU) or plaque forming units (PFU) over the weight of the composition, e.g., CFU/g.

The composition may have an initial viability of at least about $1 \times 10^9$, $1 \times 10^{10}$, $1 \times 10^{11}$ or $1 \times 10^{12}$ CFU/g, preferably at least about $1 \times 10^{10}$ CFU/g. The composition may have a predetermined viability loss under predetermined storage conditions after a predetermined period of time.

The predetermined storage conditions may include a predetermined temperature and a predetermined relative humidity (RH). The term "relative humidity (RH)" as used herein refers to the amount of water vapor in the air, often at a given temperature. Relative humidity is usually less than that required to saturate the air, and is often expressed in percentage of saturation humidity. The predetermined temperature may be at least about 25, 37, 40, 45, 50 or 55° C. The predetermined relative humidity (RH) may be at least about 10%, 20%, 30%, 33%, 35%, 40%, 50%, 60%, 70% or 80%. The predetermined conditions may be accelerated storage conditions. For example, the predetermined conditions may include about 40° C. and about 33% RH, or about 45° C. and about 33% RH.

The predetermined period of time may be at least about 1, 2, 3 or 4 weeks, or 1, 2, 3, 4, 5, 6, 12, 18, 24 or 36 months, preferably at least about 1, 2 or 3 months, more preferably at least about 1 or 3 months. A specified time period may include a shorter or longer time period that is within 10% of the specified time period. The term "3 months" as used herein refers to a time period of about 84-90 days. The term "2 months" as used herein refers to a time period of about 56-60 days. The term "1 month" as used herein refers to a time period of about 28-30 days.

In one embodiment, the composition have a viability loss of less than about 1 log unit/g under predetermined conditions after a predetermined period of time. For example, the composition may have a viability loss of less than about 1 log unit/g after about 1, 2 or 3 months at about 40° C. and 33% RH or at about 45° C. and about 33% RH.

In one embodiment, the composition has an initial viability of at least $1 \times 10^{10}$ CFU/g, and loses less than 1 log unit/g after 3 months (e.g., 84 days) at 40° C. and 33% RH. Preferably, the hydrolyzed protein is hydrolyzed pea protein or hydrolyzed casein.

The composition of the present invention may be prepared by techniques known in the art. The preparation method may include a process such as mixing, freezing, freeze-drying, ambient air drying, vacuum drying, spray drying, vacuum spray drying or a combination thereof. Preferably, no monosaccharide or disaccharide is added during the preparation of the composition. The viable microorganisms in the resulting composition, whether alone or integrated into a product such as a dietary product, possess enhanced viability when exposed to a wide range of temperatures and humidity conditions.

The microorganism used to prepare the composition of the present invention is preferably a fermentation harvest that is concentrated to a wet paste-like consistency having a solid bacterial content of about 5-30% w/v. The concentrate can be in a form of wet, frozen or thawed paste before being combined with other ingredients. Starting with a microorganism in a dry form is an alternative.

The preparation of the composition may include concentrating a selected microorganism, mixing ingredients with the concentrated microorganism to form a slurry, snap-freezing the slurry in liquid nitrogen to form particles in the form of droplets, strings or beads, drying the particles by evaporating the moisture in the particles under a regimen of reduced pressure while supplying heat to the particles. The resulting stable dry composition may be packaged or combined with other ingredients to form a product such as a pharmaceutical product, a nutraceutical supplement product, a dietary product, or an animal feed product. In particular, the resulting composition may be used to make a special dietary product such as an infant formula, a follow-on formula, processed cereal based food, canned baby food, or special food for a medical purpose.

One suitable mixing process may include adding a dry mixture of all ingredients except the microorganism in the composition directly into a concentrated culture or media solution comprising the microorganism to form a slurry. The dry mixture may be pre-dissolved in a water solution adjusted to a pH of 8-9 with a concentrated alkali solution (e.g., 1M or 5M sodium hydroxide (NaOH) solution) at 20-80° C. In the slurry, the dry weight mass of the microorganism may constitute about 5-30% w/v while the dry mixture may constitute about 20-60% or 30-50% w/v. The total solid content in the slurry may be about 25-90% or 30-60%. The amount of polysaccharides in the dry mixture may be adjusted to achieve a desired viscosity of the slurry allowing efficient drying while avoiding rubbery formation or excessive foaming that may occur during drying. A desirable density of the slurry may be achieved by any means known in the art, for example, by degassing under vacuum or injecting gas such as air, nitrogen, carbon dioxide, or argon.

The slurry may be frozen to about −30° C. or to about −80° C., or snap-frozen in liquid nitrogen by atomizing, dripping or injecting into a liquid nitrogen bath. The resulting particles in the form of beads, strings or droplets may be collected and dried in a freeze drier or vacuum drier, or alternatively stored in a deep freezer (e.g., between −30° C. and −80° C.) for later use in a frozen form or for later drying, e.g., by freeze drying or vacuum drying.

In general, helpful drying techniques include freeze drying, or evaporative drying of a thawed slurry in a vacuum oven or centrifugal evaporator while the temperature of the thawed frozen slurry or the drying product is maintained above its freezing temperature (e.g., −20 to −5° C.), followed by milling to desirable particle size. Preferably, the microorganism is coated by non-crystallized amorphous materials in the particles. The advantage of coating the microorganism with materials in an amorphous state is to increase physical stability of the particles and reduce deleterious crystalline formation within the particles. Achieving a non-crystallized amorphous structure is not a prerequisite for long term stability as some microorganisms may fare better in a more crystalline state.

The snap-frozen slurry may be loaded onto trays at a loading capacity from about 0.1 kg/sq ft to about 1.5 kg/sq ft and then immediately transferred to a vacuum drying chamber where the drying process may proceed in three major steps including: (a) an optional short temperature acclimation and structure stabilizing step of the frozen particles under a vacuum pressure of less than <1000 mTORR, (b) primary drying, or primary evaporative drying, under vacuum and at a temperature of the particles above their freezing point, and (c) secondary drying under full strength vacuum pressure and an elevated heat source temperature for a time sufficient to reduce the water activity of the resulting dry composition to, for example, about 0.3 Aw or less. The resulting dry composition may be glassy amorphous.

The terms "lyophilization" and "freeze drying" are used herein interchangeably and refer to the preparation of a composition in a dry form by rapid freezing and dehydration in a frozen state (also referred to as sublimation). Lyophilization takes place at a temperature that may results in the crystallization of ingredients in the composition.

The term "primary drying" as used herein refers to a drying step in which the temperature of a product is maintained substantially lower than the temperature of a heat source, i.e., heat source temperature or shelf temperature, to make a primarily dried product. Typically, during the primary drying step, the bulk of the moisture is removed from the product by extensive evaporation, while the product temperature is maintained above its freezing temperature but significantly lower than the temperature of the heat source.

The term "secondary drying" as used herein refers to a drying step in which the temperature of the primarily dried product is maintained near the temperature of a heat source, i.e., heat source temperature or shelf temperature, to make a dry product. This process may take place under vacuum sufficient to reduce the water activity of the resulting dry product. In a typical drying process, a secondary drying step reduces the water activity of the formulation to, for example, an Aw of about 0.3 or less.

In one embodiment, a dry composition comprising one or more viable microorganisms, at least about 50% by weight of one or more hydrolyzed proteins, one or more polysaccharides, and one or more carboxylic acid salts is prepared by a method comprising: (a) combining the viable microorganisms, the hydrolyzed proteins, the oligosaccharides, the polysaccharides and the carboxylic acid salts in an alkali aqueous solvent to form a slurry; (b) snap-freezing the slurry in liquid nitrogen to form solid frozen particles in the form of beads, droplets or strings; (c) primary drying the solid frozen particles by evaporation, under vacuum, while maintaining the temperature of the particles above their freezing temperature, whereby a primarily dried formulation is formed; and (d) secondary drying the primarily dried formulation at full strength vacuum and a heat source temperature of 20° C. or higher for a time sufficient to reduce the water activity of the primarily dried formulation to about 0.3 Aw or lower. Preferably, no monosaccharide or disaccharide is added in this method.

The preparation method of the invention may further comprise adding one or more sugars to the alkali aqueous solvent to form the slurry in step (a). The one or more sugars are selected from the group consisting of monosaccharides, disaccharides and combinations thereof. The resulting dry composition comprises less than 10% by weight of the one or more sugars.

The method may further comprise sterilizing the hydrolyzed proteins, the oligosaccharides, the polysaccharides and the carboxylic acid salts before step (a). Where monosaccharides and/or disaccharides are added in step (a), the monosaccharides and/or disaccharides may be sterilized before step (a). The sterilization may be achieved by any method known in the art. For example, heating under pressure an aqueous mixture of the hydrolyzed proteins, the oligosaccharides, the polysaccharides and the carboxylic acid salts, and followed by cooling before step (a).

The method may further comprise solubilizing the hydrolyzed proteins, the oligosaccharides, the polysaccharides and the carboxylic acid salts before step (a). Where monosaccharides and/or disaccharides are added in step (a), the monosaccharides and/or disaccharides may be solubilized before step (a).

The method may further comprise cutting, crushing, milling or pulverizing the composition into a free flowing powder. The particle size of the powder may be less than about 10,000, 1,000, 500, 250 or 100 µm, preferably less than about 1,000 µm, more preferably less than about 250 µm.

The composition of the present invention may be used directly as a flake, or grounded into a powder and sieved to an average particle size of about 1-10,000 µm, preferably 10-1,000 µm.

The composition of the present invention may be administrated as a concentrated powder or a reconstituted liquid (e.g., a beverage). It may also be incorporated either in flake or powder form into an existing food product.

The method may further comprise making a pharmaceutical product, a nutraceutical supplement product, a dietary product, or an animal feed product with the composition of the present invention, which comprises an effective amount of one or more probiotic microorganisms for providing a probiotic benefit to a host in the product. Examples of a special dietary product may include an infant formula, a follow-on formula, processed cereal based food, canned baby food, and special food for a medical purpose. Preferably, the special dietary product is an infant formula.

The resulting dry stable powder comprising viable microorganisms may be agglomerated with molten fats. The dry powder may be placed in a planetary mixer at 40-50° C., and molten fats such as cocoa butter, natural waxes or palm oil, stearic acid, stereane or a mixture thereof may be added slowly to the warm powder. The mixture may be cooled down to below the melting temperature of the fats while mixing continues until a visually uniform size of agglomerated powder is achieved. The weight mass of the molten fats in the resulting composition may be about 20-70%, preferably 30-50%.

Example 1. Stability of Dry Probiotic Product Containing Trehalose Only as a Cryo-Protectant A concentrated harvest of *Bifidobacterium* sp. was added with 10% w/w trehalose and snap frozen in liquid nitrogen. The resulting frozen beads were freeze dried to a dry product under full vacuum for 48 h without heating. The initial viability of the dry product was 11.63 log CFU/g. A sample of this dry product was placed under accelerated stability challenge at 40° C. and 33% RH, and showed a viability loss of 1.46 log unit/g after 14 days and a viability loss of 3.17 log unit/g after 28 days. These results demonstrates the inherent instability of a dry sample containing live microorganisms and trehalose as the only cryo-protectant.

Example 2. Preparation of Dry Probiotic Composition

A dry probiotic composition according to the present invention was prepared. Hydrolyzed pea protein (75 g, Friesland Capina Doma, Paramus, N.J.) was dissolved in 100 ml warm distilled water at 75° C. The pH of the resulting pea solution was adjusted to 8.5 using a 20% concentrated NaOH solution. Locust Bean gum (3 g, Tic gum, Belcamp, Md.), inulin (17 g instant inulin containing 7% sugars, Cargill Minneapolis, Minn.), and sodium ascorbate (5 g, Sigma) were dry blended and added to the pea solution under continuous mixing at 700 rpm in an impeller mixer. The resulting mixture was cooled down and maintained at a temperature between 35° C. and 40° C. under continuous mixing.

The resulting mixture was translucent with a consistency of syrup and amber in color. The liquid mixture was transferred to a dual planetary mixer (DPM, 1 qt, Ross Engineering, Inc. Savannah, Ga.) equipped with a controlled temperature jacket. The mixer jacket temperature was at ambient temperature or lower. Frozen probiotic bacteria *Bifidobacterium* sp. concentrate (120 g, containing 10% w/w bacterial solids) was added under mixing at 20 rpm over 2-3 minutes, or until all the bacteria were well thawed and homogenously distributed. The probiotic slurry was cooled down to 4° C. and kept at this temperature for 30-60 minutes. The slurry was then dripped and snap-frozen in a liquid nitrogen bath to form frozen beads, which were harvested from the liquid nitrogen and stored at −80° C. for later drying.

For drying, the frozen beads were spread on pre-cooled trays (−20° C.) at a loading capacity of 800 g/sq ft and then immediately placed on shelves in a freeze drier (Model 25 SRC, Virtis, Gardiner, N.Y.). The primary drying step was initiated by adjusting the vacuum between 900-1500 mTORR and the shelf temperature raised to 20° C. These primary drying temperature and vacuum pressure settings were maintained for 16 hours. Before primary drying, the temperature of the frozen beads was optionally acclimatized to about −20° C. by applying a vacuum pressure at about 1000 mTORR with no heat to allow the temperature of the frozen beads to stabilize at about −20° C. for about 10 minutes. The optional acclimation step was then followed by a primary drying step by adjusting the vacuum pressure to 900-1500 mTORR and the shelf temperature to +20° C. These temperature and vacuum pressure settings were maintained for about 16 hours. After the primary drying step, a secondary drying step followed at full strength vacuum (i.e., 150-200 mTORR) and the shelf temperature was raised to 40° C. for an additional 8 hours. As a result, the composition was completely dried and its water activity as measured by a Hygropalm Aw1 instrument (Rotonic Instrument Corp., Huntington, N.Y.) was below Aw 0.3. The dry material was then milled and sieved to particle size 250 µm and stored at 4° C.

Example 3. Comparison of Storage Stability

The dry probiotic product of Example 1 and the dry probiotic composition of Example 2 were each mixed with an equal amount of maltodextrin (1:1 ratio) and placed in a desiccator under accelerated storage conditions. Samples were taken periodically for microbial CFU assessment using standard microbiological dilutions and LMRS agar plating procedures.

FIG. 1 shows the storage stability results under accelerated storage conditions of 40° C. and 33% RH for the dry probiotic product of Example 1 (unstabilized *Bifidobacterium* sp.) and the dry probiotic composition of Example 2 (stabilized *Bifidobacterium* sp.). The dry probiotic product of Example 1 completely lost its viability within the first few weeks while the dry probiotic composition of Example 2 according to the present invention lost only 0.49 log unit/g after 84 days.

Figure 2:
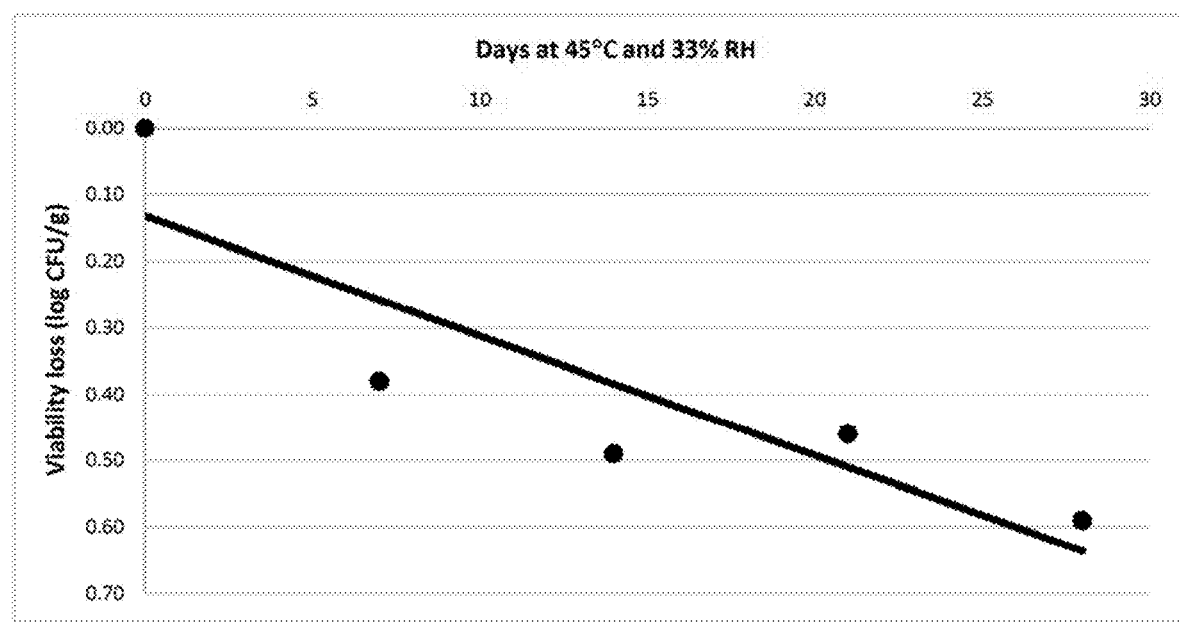
FIG. 2 shows storage stability of stabilized dry probiotic product prepared according to Example 2 under accelerated storage conditions of 45° C. and 33% RH.

FIG. 2 shows the storage stability under accelerated storage conditions of 45° C. and 33% RH for the dry probiotic composition of Example 2 (stabilized *Bifidobacterium* sp.). The dry probiotic composition of Example 2 according to the present invention lost only 0.59 log unit/g after 30 days.

Example 4. Effects of Disaccharides on Stability

The effects of disaccharide lactose on stability of a dry probiotic composition of the present invention were evaluated. Five dry compositions were prepared by mixing dry ingredients, including increasing amounts of lactose and proportionally reducing amounts of hydrolyzed pea protein, with frozen probiotic bacteria *Bifidobacterium* sp. (120 g, containing 10% w/w bacterial solids) using the method described in Example 2 and then tested for stability using the method described in Example 3. Table 1 shows the weight percentage (w/w) of each ingredient as well as the initial viability (log units of CFU/g) and the viability loss (loss of log units of CFU/g) after 1 month for Composition Nos. 1-3 or 3 months for Composition Nos. 4-5 at 40° C. and 33% RH. Composition No. 4 (with 8.9% w/w lactose and 58% w/w hydrolyzed pea protein) and Composition No. 5 (with 66.9% w/w hydrolyzed pea protein and no lactose) showed less than one (1) log unit of CFU/g loss after 84 days at 40° C. and 33% RH. Composition Nos. 1-3 (with 17% w/w or more lactose and 49.1% w/w or less hydrolyzed pea protein) each showed a viability loss of over one (1) log unit of CFU/g after 1 month at 40° C. and 33% RH.

were prepared by mixing dry ingredients, including sodium ascorbate in Composition Nos. 3-5, sodium citrate in Composition No. 6), and Vitamin E in Composition Nos. 2-4, with frozen probiotic bacteria *Bifidobacterium* sp. (120 g, containing 10% w/w bacterial solids) using the method described in Example 2 and then tested for stability using the method described in Example 3. Table 2 shows the weight percentage (w/w) of each ingredient, as well as the initial viability (log units of CFU/g) and the viability loss (loss of log units of CFU/g) after 84 days at 40° C. and 33% RH for each resulting dry composition. Composition Nos. 3-6 (with 0.9-4.5% w/w sodium ascorbate or 4.5% w/w sodium citrate) showed less than one (1) log unit of CFU/g loss after 84 days at 40° C. and 33% RH.

TABLE 2

Effect of carboxylic acid salt on stability (% w/w)

| # | Bacterial solids | Hydrolyzed pea protein | Inulin | Locust bean | Ascorbate | Vitamin E | Initial viability | Viability loss |
|---|---|---|---|---|---|---|---|---|
| 1 | 10.7 | 69.5 | 16.1 | 2.7 | 0 | 0 | 11.22 | 1.31 |
| 2 | 10.7 | 66.9 | 15.2 | 2.7 | 0 | 4.5 | 11.23 | 1.47 |
| 3 | 10.7 | 66.9 | 15.2 | 2.7 | 0.9 | 3.6 | 11.32 | 0.87 |
| 4 | 10.7 | 66.9 | 15.2 | 2.7 | 2.25 | 2.25 | 11.14 | 0.48 |
| 5 | 10.7 | 66.9 | 15.2 | 2.7 | 4.5 | 0 | 11.25 | 0.49 |
| 6 | 10.7 | 66.9 | 15.2 | 2.7 | 4.5 citrate | 0 | 11.15 | <1 |

Example 6. Effects of Oligosaccharides on Stability

The effects of oligosaccharides, inulin, short chain oligosaccharides and gamma cyclodextrin, on stability of a dry probiotic composition of the present invention were evaluated. Compositions containing 75 g casein hydrolysate (DMV international Amersfoort, the Netherlands), 17 g cyclodextrin (Wacker, Munchen, Germany) or 17 g inulin (instant inulin containing 7% sugars, Cargill Minneapolis, Minn.), or 17 g short chain oligosaccharides (Orafti P-95 containing 5% sugars, Beneo, Tienen, Belgium), 3 g gum Arabic (Tic gum, Belcamp, Md.) and 5 g mixture of sodium citrate and sodium ascorbate (1:1 w/w, Sigma) were prepared using the method described in Example 2 and tested for stability using the method described in Example 3. The

TABLE 1

Effect of Lactose on Stability (% w/w)

| # | Bacterial solids | Hydrolyzed pea protein | Lactose | Inulin | Locust Bean | Sodium Ascorbate | Vitamin E | Initial Viability | Viability loss |
|---|---|---|---|---|---|---|---|---|---|
| 1 | 10.7 | 42.8 | 26.8 | 13.4 | 1.8 | 0.9 | 3.6 | 10.91 | 1.29 |
| 2 | 10.7 | 44.7 | 31.2 | 6.2 | 2.7 | 0.9 | 3.6 | 10.94 | 1.96 |
| 3 | 10.7 | 49.1 | 17.8 | 15.2 | 2.7 | 0.9 | 3.6 | 11.00 | 1.23 |
| 4 | 10.7 | 58 | 8.9 | 15.2 | 2.7 | 0.9 | 3.6 | 10.78 | 0.7 |
| 5 | 10.7 | 66.9 | 0 | 15.2 | 2.7 | 0.9 | 3.6 | 11.32 | 0.87 |

Example 5. Effects of Carboxylic Acid Salt on Stability

The effects of carboxylic acid salts, sodium ascorbate and sodium citrate, on stability of a dry probiotic composition of the present invention were evaluated. Six dry compositions resulting dry composition prepared with the short chain oligosaccharides comprised less than 1% w/w monosaccharides and/or disaccharides. All these compositions resulted in an initial viability (log units of CFU/g) ranging from 11.2 to 11.3 log CFU/g, and a viability loss ranging from 0.43 to 0.66 log CFU/g after three months at 40° C. and 33% RH.

Example 7. Effects of Polysaccharides

The effects of polysaccharides, locust bean gum, gum Arabic, carrageenan and alginate, on stability of a dry probiotic composition of the present invention were evaluated. Compositions containing 75 g casein hydrolysate (DMV international Amersfoort, the Netherlands), 17 g cyclodextrin (Wacker, Munchen, Germany) 3 g gum Arabic (Tic gum, Belcamp, Md.), or 3 g locust bean gum (Tic gum, Belcamp, Md.), or 3 g alginate (FMC BioPolymer, Philadelphia, Pa.), or 3 g carrageenan (Tic gum, Belcamp, Md.), and 5 g mixture of sodium citrate and sodium ascorbate (1:1 w/w, Sigma) were prepared using the method described in Example 2 and then tested for stability using the method described in Example 3. All these compositions resulted in an initial viability (log units of CFU/g) ranging from 11.2 to 11.3 log CFU/g, and a viability loss ranging from 0.46 to 0:81 log CFU/g after three months at 40° C. and 33% RH.

Example 8. Effects of Protein Source

The effects of protein source, pea protein hydrolysate, casein hydrolysate and wheat protein hydrolysate, on stability of a dry probiotic composition of the present invention were evaluated. Compositions containing 65 g casein hydrolysate (DMV international Amersfoort, the Netherlands) or wheat hydrolysate (Marcor Development Corp., Carlstadt, N.J.) or pea protein hydrolysate (Friedsland Campina Domo, Paramus, N.J.), 27 g cyclodextrin (Wacker, Munchen Germany) 3 g gum Arabic (Tic gum, Belcamp, Md.) and 5 g mixture of vitamin E and sodium ascorbate (4:1 w/w, Sigma), and a composition containing 75 g soy hydrolysate (Sigma), 17 g inulin (instant inulin containing 7% sugars, Cargill Minneapolis, Minn.) 3 g locust bean gum (Tic gum, Belcamp, Md.) or 3 g alginate (FMC BioPolymer, Philadelphia, Pa.), or 3 g carrageenan (Tic gum, Belcamp, Md.) and 5 g mixture of sodium citrate and sodium ascorbate (1:1 w/w, Sigma) were prepared using the method described in Example 2 and then tested for stability using the method described in Example 3. The six resulting dry compositions showed an initial viability of 11.01-11.34 log units CFU/g. While the resulting composition comprising pea hydrolysate or soy hydrolysate or casein hydrolysate showed 0.51-0.81 log unit/g loss after 84 days at 40° C. and 33% RH, the composition comprising wheat protein hydrolysate lost 2.01 log units/g.

Example 9. Stability of Various Probiotic Bacteria Species

The stability of various probiotic bacteria, *L. acidophilus*, and *Bifidobacterium* sp., in a dry probiotic composition of the present invention was evaluated. Compositions containing 75 g pea protein hydrolysate (Friedsland Campina Domo, Paramus, N.J.), 17 g inulin (Cargill Minneapolis, Minn.), 3 g locust bean gum (Tic gum, Belcamp, Md.) and 5 g mixture of sodium citrate and sodium ascorbate (1:1 w/w, Sigma) were prepared using the method described in Example 2 and then tested for stability using the method described in Example 3. The initial viability (log units of CFU/g) of the *L. acidophilus* composition was 10.57 log CFU/g, and a viability loss of 0.64 log units/g loss after three months at 40° C. and 33% RH. The initial viability (log units of CFU/g) of the *Bifidobacterium* sp., composition was 11.11 log CFU/g, and a viability loss of 0.41 log units/g loss after three months at 40° C. and 33% RH.

Example 10. Infant Formula

A stable dry composition comprising live *Bifidobacterium* sp. was prepared and sieved to particle size of 50-250 µm according to Example 2. An infant formula comprising probiotic bacteria was prepared by mixing 19.9 g of Gerber Good Start (Nestle Infant Nutrition, Florham Park, N.J.) with 0.1 g of the dry composition particles in the size range between 50 µm and 250 µm. The final product contains 8.03 log CFU/g of *Bifidobacterium* sp.. The probiotic infant formula were packed into closed 180 cc HDPE bottles and exposed to controlled temperature of 25° C. and 40° C. The water activity inside the bottles was Aw-0.2). The product was subjected to monthly microbiological stability testing over a period of 9 months or until a reduction in the assay count below 1 log CFU/g was observed. The viability loss of *Bifidobacterium* sp in the infant formula product stored at 25° C. and 40° C. was 0.09 and 0.82 log CFU/g, respectively.

Example 11. Probiotic Supplement

A stable dry composition comprising *Lactobacillus acidophilus* will be prepared according to Example 2 and formulated into oral dosage forms, such as tablets, caplets, or capsules. Orange flavored tablets containing 19.9 g of a compression agent (dextrose) and 0.1 g of the dry formulation particles in the size range between 50 µm and 250 µm will be prepared by direct compression on a rotary tableting machine using a ½" round standard concave tooling. The final product will contain about 5E+8 CFU/unit dose. Hardness of the tablets is in the range of 8-10 kp and disintegration times will be approximately 20 second. The compressed tablets will be packaged into 180 cc HDPE bottles of 100 tablets each and exposed to controlled temperature/humidity of 40° C./33% RH. The product will be subjected to monthly microbiological stability testing over a period of 12 months or until a reduction in the assay count below 1E+6 CFU/unit dose is observed.

Example 12. A Functional Beverage Drink

A stable dry composition comprising *Lactobacillus acidophilus* will be prepared according to Example 2 and formulated into a dry mix containing (% by weight) 71% sucrose, 14% maltodextrin, 10% inulin, 2% dextrose, 1% citric acid anhydrous, 0.3% gum acacia, 0.3% flavors, 0.3% Tricalcium phosphate and 0.1% dry probiotic composition particles (*L. acidophilus*) in the size range between 50 µm and 250 µm. The final product will contain about 1E+9 CFU/unit dose (30 g dry mix). The product will be packaged in small aluminum foil bags (1 unit dose/bag) for drinking by stirring in 340 ml water. The beverage dry mix containing the probiotic will be subjected to monthly microbiological stability testing over a period of 12 months or until a reduction in the assay count below 1E+7/unit dose is observed.

Example 13. Multivitamins/Probiotic Tablets

Ten (10) g of dry powder composition containing the probiotic L. *Casei* will be produced as described in Example 2. For tableting, the dry and stable probiotic composition (100 mg) will be mixed with 400 mg of commercially available multivitamins powder (Centrum®, Pfizer) containing 2% w/w magnesium stearate and 2% w/w hydrophilic fumed silica (AEROSIL® 200, Evonik Industries) and compressed in hand held pill press equipment (using a ½" tablet diameter housing). Each tablet will contain about 1E+7 CFU/tablet). The tablets will be packaged into 180 cc HDPE bottles of 100 tablets each and exposed to controlled temperature/humidity of 40° C./33% RH. The bottles will be subjected to monthly microbiological stability testing over a period of 12 months or until a reduction in the assay count below 1E+6 CFU/tablet is observed.

Example 14. Seed Inoculant Microbes

A biological control agent such as Rhizobacteria will be prepared in dry composition according to Example 2. The effectiveness of the dry Rhizobacteria composition will be evaluated on soybean coated with the dry composition powder at 1E+6 CFU/seed. The coated seeds will be packaged in paper bags and maintained at room temperature (23-25° C.). The bags will be subjected to monthly microbiological stability testing over a period of 12 months or until a reduction in the assay count below 1E+5 CFU/seed is observed.

Example 15. Probiotic Pet Food

A commercially available pelleted pet food for dogs will be dried in a convection oven to a water activity of 0.1, and then coated with stable *L. acidophilus* dry composition prepared as described in Example 2. The dry pellets will be sprayed with about 5% of fat-based moisture barrier (a mixture of 40% chicken fat, 40% cocoa butter and 20% beeswax), mixed in a drum tumbler with the dry powder formulation (usually 0.1-0.5% of the total pet food that provides a dosage of 1E+8 CFU/g), and finally sprayed with additional coat of the fat-based moisture barrier. The total amount of coating will be about 15% (of the pet food). Coating time will be about 30 min.

Example 16. Fish Feed

Pelleted probiotic feed for fish according to the present invention will be prepared with a mixture of several probiotics. A stable dry probiotic composition containing a mixture of L. *Rhamnosus*, L. *Acidophilus* and *Bifidobacterium lactis* will be prepared as described in Example 2. A commercially available starter feed for salmon (Zeigler Bros., Gardners, Pa.) will be first dried in a convection oven to a water activity of 0.1, and then coated with the probiotics composition in a drum tumbler. The feed pellets (1000 g) will be first sprayed with about 5% by weight of fat-based moisture barrier (a mixture of 40% fish oil, 40% cocoa butter and 20% beeswax), then mixed with 1 g of the stable dry probiotic composition (to attain a dosage of 1E+7 CFU/g feed), and finally sprayed with additional coat of the fat-based moisture barrier. The total amount of coating will be about 10% (of the fish feed).

Example 17. Animal Feed

About 500 g of commercially available animal feed for either steers or chickens will be top coated in a drum tumbler with 3% oil mixture containing one portion of dry stable *L. acidophilus* composition prepared as described in Example 2, and two (2) portions of plant oil such as corn oil. The CFU count of the probiotic bacteria will be about 1E+9/g feed. The coated feed will be placed in a 43% relative humidity chamber at 40° C. and after 14 days storage in these extreme conditions; the viability loss of the probiotic bacteria is expected to be less than one (1) log unit of the initial CFU counts. Another probiotic coated feed will be placed in a 33% relative humidity chamber at 30° C. and after six (6) month storage in these conditions; the viability loss of the probiotic bacteria is expected to be less than one (1) log unit of the initial CFU.

Example 18. Dry Composition Containing Live Phages Against *Vibrio anguillarum*

Ten (10 g) of stable composition containing live phages will be prepared as described in Example 2. The dry live phages composition will be mixed with 20 g of fish oil and the suspension coated on 1 kg tilapia feed pellets. The coated feed will be stored under typical warehouse storage conditions. The viability of the phages in the fish feed is expected to be preserved after 14 days exposure in high humidity and non-refrigerated storage conditions when using the compositions and methods of the present invention.

These examples demonstrates that different microorganisms, such as probiotic bacteria, fungi and viruses used for treating various animals including human, fish, chickens, Swaine and companion animals, can be preserved in the composition and drying methods of the present invention and then coated or mixed in food or feeds for long term storage on shelf or for at least two (2) weeks in a feeding hopper under typical humid and temperature conditions that uncoated feed is stored.

The term "about" as used herein when referring to a measurable value such as an amount, a percentage, and the like, is meant to encompass variations of ±20% or ±10%, more preferably ±5%, even more preferably ±1%, and still more preferably ±0.1% from the specified value, as such variations are appropriate.

All documents, books, manuals, papers, patents, published patent applications, guides, abstracts, and other references cited herein are incorporated by reference in their entirety. Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

What is claimed is:

1. A dry composition comprising one or more viable microorganisms, at least 50% by weight of one or more hydrolyzed proteins, less than 5% by weight of one or more sugars selected from the group consisting of monosaccharides, disaccharides and combinations thereof, and one or more carboxylic acid salts, each percentage based on the total weight of the dry composition, wherein the hydrolyzed protein is selected from the group consisting of hydrolyzed pea, casein, soy protein and combinations thereof.

2. The composition of claim 1, wherein the one or more viable microorganisms are selected from the group consisting of live bacteria, fungi, yeast, unicellular algae, viruses and phages.

3. The composition of claim 2, wherein the bacteria are probiotic bacteria.

4. The composition of claim 1, wherein the one or more hydrolyzed proteins are selected from the group consisting of milk proteins, plant proteins, and combinations thereof.

5. The composition of claim 1, wherein the one or more hydrolyzed proteins are selected from the group consisting of hydrolyzed casein, hydrolyzed pea protein, and combinations thereof.

6. The composition of claim 1, further comprising one or more oligosaccharides.

7. The composition of claim 6, wherein the composition comprises 5-30% by weight of the one or more oligosaccharides based on the total weight of the dry composition.

8. The composition of claim 6, wherein the one or more oligosaccharides are selected from the group consisting of inulin, short chain oligosaccharides, cyclodextrins, maltodextrins, dextrans, fructo-oligosaccharides (FOS), galacto-oligosaccharides (GOS), mannan-oligosaccharides (MOS), and combinations thereof.

9. The composition of claim 6, wherein the one or more oligosaccharides are inulin, short chain oligosaccharides or cyclodextrin.

10. The composition of claim 1, further comprising one or more polysaccharides.

11. The composition of claim 10, wherein the composition comprises 1-10% by weight of the one or more polysaccharides based on the total weight of the dry composition.

12. The composition of claim 10, wherein the one or more polysaccharides are selected from the group consisting of alginate, gum acacia, locust bean gum, carrageenan, starches, modified starches, and combinations thereof.

13. The composition of claim 1, wherein the composition comprises 1-10% by weight of the one or more carboxylic acid salts based on the total weight of the dry composition.

14. The composition of claim 1, wherein the one or more carboxylic acid salts are one or more salts of a carboxylic acid selected from the group consisting of lactic acid, ascorbic acid, maleic acid, oxalic acid, malonic acid, malic acid, succinic acid, citric acid, gluconic acid, glutamic acid, and combinations thereof.

15. The composition of claim 1, wherein the one or more carboxylic acid salts are selected from the group consisting of ascorbic acid salts, citric acid salts, and combinations thereof.

16. The composition of claim 1, wherein the composition has viability of at least $1 \times 10^{10}$ CFU/g, and wherein the composition has a viability loss of less than 1 log unit/g after 3 months at a temperature of 40° C. and a relative humidity of 33%.

17. The composition of claim 16, wherein the one or more hydrolyzed protein is hydrolyzed pea protein or hydrolyzed casein.

18. The composition of claim 1, further comprising 1-5% w/w of vitamin E based on the total weight of the dry composition.

19. The composition of claim 1, further comprising one or more oligosaccharides and one or more polysaccharides.

20. A method for preparing a dry composition comprising one or more viable microorganisms, at least 50% by weight of one or more hydrolyzed proteins, less than 5% by weight of one or more sugars selected from the group consisting of monosaccharides, disaccharides, and combinations thereof, and one or more carboxylic acid salts, each percentage based on the total weight of the dry composition, wherein the hydrolyzed protein is selected from the group consisting of hydrolyzed pea, casein, soy protein, and combinations thereof, comprising:
(a) combining the one or more viable microorganisms, the one or more hydrolyzed proteins, the one or more sugars and the one or more carboxylic acid salts in an alkali aqueous solvent to form a slurry;
(b) snap-freezing the slurry in liquid nitrogen to form solid frozen particles in the form of beads, droplets or strings;
(c) primary drying the solid frozen particles by evaporation, under vacuum, while maintaining the temperature of the particles above their freezing temperature, whereby a primarily dried formulation is formed; and
(d) secondary drying the primarily dried formulation at full strength vacuum and a heat source temperature of 20° C. or higher for a time sufficient to reduce the water activity of the primarily dried formulation to 0.3 Aw or lower, whereby the composition is prepared.

21. The method of claim 20, further comprising adding one or more oligosaccharides and one or more polysaccharides to the alkali aqueous solvent to form the slurry in step (a).

22. The method of claim 21, further comprising sterilizing the one or more hydrolyzed proteins, the one or more oligosaccharides, the one or more polysaccharides, one or more carboxylic acid salts, and the one or more sugars before step (a).

23. The method of claim 20, further comprising making a product with the composition, wherein the product is selected from the group consisting of pharmaceutical products, nutraceutical products, food products, feed products, and special dietary products.

\* \* \* \* \*